(12) United States Patent
Serino et al.

(10) Patent No.: US 7,235,094 B2
(45) Date of Patent: Jun. 26, 2007

(54) VASCULAR PROSTHESIS FOR THE TREATMENT OF ABDOMINAL AORTIC ANEURYSMS, USING A COMBINED LAPAROSCOPIC/OPEN AND ENDOVASCULAR TECHNIQUE, AND DELIVERY SYSTEM FOR RELEASING A PROSTHESIS FITTED WITH ANCHORING STENTS

(75) Inventors: Francesco Serino, Rome (IT); Mauro Ferrari, Pisa (IT)

(73) Assignee: Bolton Medical, Inc., Sunrise, FL (US)

( * ) Notice: Subject to any disclaimer, the term of this patent is extended or adjusted under 35 U.S.C. 154(b) by 187 days.

(21) Appl. No.: 10/718,315

(22) Filed: Nov. 20, 2003

(65) Prior Publication Data

US 2004/0111145 A1   Jun. 10, 2004

(30) Foreign Application Priority Data

Nov. 27, 2002   (IT) .......................... RM2002A0596

(51) Int. Cl.
*A61F 2/06* (2006.01)
*A61M 29/00* (2006.01)

(52) U.S. Cl. .................. 623/1.11; 623/1.23; 623/1.25; 606/194

(58) Field of Classification Search ................ 606/108, 606/190–198, 159; 623/1.11, 1.23, 1.35, 623/1.13, 1.14; 604/96.01–109, 533–535; 600/201, 204, 207

See application file for complete search history.

(56) References Cited

U.S. PATENT DOCUMENTS

| | | | | |
|---|---|---|---|---|
| 5,275,622 A | * | 1/1994 | Lazarus et al. | 623/1.11 |
| 5,507,769 A | * | 4/1996 | Marin et al. | 606/198 |
| 5,697,948 A | * | 12/1997 | Marin et al. | 606/198 |
| 5,733,299 A | * | 3/1998 | Sheiban et al. | 606/192 |
| 6,143,014 A | * | 11/2000 | Dehdashtian et al. | 606/192 |
| 6,423,032 B2 | * | 7/2002 | Parodi | 604/103.07 |

* cited by examiner

*Primary Examiner*—Glenn K. Dawson
*Assistant Examiner*—Amanda Adams
(74) *Attorney, Agent, or Firm*—Mayback + Hoffman, P.A.; Gregory L. Mayback (57) ABSTRACT

A bifurcated vascular prosthesis implanted using a combined laparoscopic/open and endovascular technique for curing aneurysms of the abdominal aorta includes two stents on distal arms of the prosthesis. A delivery system and surgical kit for the release of the vascular prosthesis includes a pair of balloon release catheters, to be inserted within each corresponding stent and to remain adhering thereto throughout the time prior to release until reinflated with an inflating syringe, and a pair of balloon guide catheters, each including a dilator and a sheath. A method for implanting the prosthesis is also provided.

12 Claims, 6 Drawing Sheets

VASCULAR PROSTHESIS FOR THE TREATMENT OF ABDOMINAL AORTIC ANEURYSMS, USING A COMBINED LAPAROSCOPIC/OPEN AND ENDOVASCULAR TECHNIQUE, AND DELIVERY SYSTEM FOR RELEASING A PROSTHESIS FITTED WITH ANCHORING STENTS

BACKGROUND OF THE INVENTION

Field of the Invention

The present invention relates to a vascular prosthesis for the treatment of abdominal aortic aneurysms, using a combined laparoscopic/open and endovascular technique. The present invention also relates to a delivery system for the release of a prosthesis fitted with anchoring stents, such as the above-mentioned vascular prosthesis or other prostheses.

Aneurysm of the abdominal aorta is a degenerative disease of the vessel that results in dilation and, sometimes, fatal rupture. In the past, when this disease was diagnosed, open surgery was generally performed to repair the damaged vascular section and, therefore, to prevent rupture of the vessel.

Traditionally, open surgery includes resection of the aneurysm and the implantation of a bifurcated prosthesis. The bifurcated prosthesis is made of a suitable tissue, such as polytetrafluoroethylene (PTFE) or DACRON®, which is the trade name of a particular polyester fiber from DUPONT®. The approach is through a large abdominal incision, opening the aneurysm after upstream and downstream closure (clamping) of the aorta (consequently preventing circulation in the lower part of the body for the duration of the procedure), suturing the holes of the lumbar arteries from inside the abdominal aorta, and suturing of the abovementioned prosthesis to the healthy parts. This procedure, which has been in use for decades, is particularly invasive, is associated with long convalescence and major general risks, and is, undoubtedly, a long-lasting procedure with full rehabilitation of the patient.

An endovascular technique, providing for the application of an endoprosthesis, that is, a prosthesis inserted within the vessels, with access from the inguinal arteries, and, therefore, without "opening" of the abdomen, was introduced some ten years ago. Such a prosthesis expands within the aneurysm, bearing against the healthy parts to which it is fixed through the effect of the radial force exerted by stents, or expandable metal retaining members, which are sutured or fixed to the conventional tissue prosthesis (DACRON® or PTFE). This is a very clear example of mini-invasive surgery, but, unfortunately, there are limits to its application and inherent problems.

The limitations upon the endovascular technique are determined by the anatomical conformation of the part referred to as the proximal neck of the aorta, that is, the healthy cranial part against which the endoprosthesis is supported. In fact, it is specifically the unsuitability of an excessively short, calcified, or angled neck of the aorta that is one of the most frequent reasons why the endovascular treatment is ruled out for patients.

The problems of the endovascular technique have been observed over the passage of time, and are associated with the intrinsic nature of the product and the implantation technique, migration of the prosthesis, the breakage of the metal parts due to stress corrosion, or loss of seal with refill of the aneurysm (referred to as endo-leak) and ultimately rupture some distance away. "Refill" of the aneurysm may occur either through loss of contact of the prosthesis with the arterial wall or through disconnection of its parts, and, also and more frequently, it is due to the persistent patency of the lumbar arteries. In addition to the need for further surgery with additional corrections, or even removal of the endoprosthesis and repair through delayed conventional procedures, these problems make it necessary to subject all surgery patients to undergo periodical checks (a CT scan every 6 months) for the rest of their lives. In a search for alternative techniques of a mini-invasive nature that, nevertheless, guarantee the same efficiency and durability as the conventional procedure, a laparoscopic technique that combines the good results of implanting conventional prostheses, with reduced trauma in comparison with the conventional technique, has been developed quite recently. In fact, the laparoscopic technique makes it possible to open the aorta, suture the lumbar arteries, and "sew on" conventional prostheses, which, therefore, provide a guaranteed seal. Such a technique does not involve any, or only minimum, cutting of the abdomen, over a length of a few centimeters, obtaining access to the abdomen through simple "holes" through which optic fibers, to provide a video view of the site of the operation, or "ad hoc" constructed instruments, are passed. Although such a technique resolves the problems of invasiveness, in that, patients can have a very short convalescence and negligible inconvenience, there are, nevertheless, a number of limitations associated with the longer duration of the procedure, due to the difficulty of operating in restricted spaces. In addition, to be able to restrict the incision (laparotomy) to only 7 to 8 centimeters, there is a technical difficulty in gaining access to the iliac arteries, to which the two limbs of the prosthesis are sutured.

SUMMARY OF THE INVENTION

It is accordingly an object of the invention to provide a vascular prosthesis implanted using a combined laparoscopic/open and endovascular technique for curing aneurysms of the abdominal aorta and delivery system for releasing a prosthesis fitted with anchoring stents that overcome the hereinafore-mentioned disadvantages of the heretofore-known devices and methods of this general type and that provides a vascular prosthesis that can be implanted through a mini-laparotomy and, thus, with reduced invasiveness, that provides a vascular prosthesis having iliac branches with stents that can be inserted in the iliac arteries from inside the opened aortic aneurysm, pulled from the femoral arteries, and endovascularly sealed to the iliac arteries by inflating the two balloons inside the stents, thus, reducing the times for isolation of the iliac arteries and suture of the branches.

With the foregoing and other objects in view, there is provided, in accordance with the invention, a bifurcated vascular prosthesis for implantation through a combined laparoscopic/open and endovascular technique for curing aneurysms of the abdominal aorta, including a tubular body having a lower extremity and an upper proximal extremity to be sutured to a proximal neck of the aorta, a pair of tubular branches diverging downwards from the lower extremity of the body and ending in corresponding distal portions, the tubular body and the tubular branches being of a vascularly usable material, and retaining members secured to the distal portions.

In accordance with another feature of the invention, the retaining members are two stents. Each of the stents can be formed of a tubular portion of expandable metal mesh of a biocompatible material. Each of the stents can be fixed respectively within each extremity of the distal portions and can be at least partly covered by the material.

With the objects of the invention in view, there is also provided a bifurcated vascular prosthesis for implantation through a combined laparoscopic/open and endovascular technique for curing aneurysms of the abdominal aorta, including a Y-shaped prosthesis body of a material usable in animal vessels having a body portion with a lower extremity and an upper extremity to be sutured to a proximal neck of the aorta and a tubular branches respectively diverging away from the lower extremity and ending in corresponding distal portions, and retaining members secured to the distal portions.

With the objects of the invention in view, there is also provided a delivery system for the release of a prosthesis fitted with anchoring stents including:

a pair of releasing balloon catheters each having a small tube with two opposite ends, one end of the small tube being provided with a balloon intended to be inserted within the corresponding stents of the vascular prosthesis and to remain adhering thereto throughout the time prior to release, and the opposite end of the small tube being provided with a portion suitable for connecting to an inflating syringe;

a pair of inflating syringes provided with a connection to the release catheter for inflating the balloons to achieve release of the stents;

a pair of guiding balloon catheters each including a dilator and a sheath;

the dilator, which has an inner lumen with a diameter suitable for passage of the small tube of the releasing catheter, having a proximal portion, a median portion, and a distal portion, the proximal portion, of larger outside diameter, being provided with a haemostatic valve, the median portion having a constant outside diameter less than that of the proximal portion, and the elongated distal portion tapering for retrieval in the aorta; and the sheath being a tubular member with an inside diameter slightly greater than that of the median portion of the dilator and having an outer terminal balloon corresponding to a distal end thereof, the balloon being connected to a small tube running outside and eccentrically with respect to the tubular member and terminating in a portion suitable for connecting to an inflating syringe; and conventional valved introducers for each balloon guide catheter.

With the objects of the invention in view, there is also provided a delivery system for release of a prosthesis having anchoring stents, including a pair of releasing balloon catheters each having an inflatable balloon adapted to be removably inserted within a portion of the prosthesis, a self-supporting tube defining a lumen and having a first diameter and two opposing ends, a cup connection having a second diameter greater than the first diameter, the cup connection being disposed at a first of the ends and connecting the inflatable balloon to the tube for fluidically connecting the lumen with the inflatable balloon to pass liquid to inflate the inflatable balloon, and a terminal connection fluidically connected to the lumen at a second of the ends, a pair of inflating syringes each having a connection for releasable attachment to the terminal connection of a respective one of the releasing catheters and, when connected thereto, fluidically connecting a respective one of the syringes to the inflatable balloon, a pair of guiding balloon catheters each having a dilator defining an inner lumen having an inside third diameter sized to pass the tube of the release catheter therethrough, the dilator having a proximal portion having an outside fourth diameter larger than the third diameter, a median portion having a constant outside fifth diameter smaller than the outside fourth diameter, and a distal portion tapering for insertion into a vessel, and a tubular sheath having distal ends, an inside sixth diameter at least as great as the outside fifth diameter of the median portion of the dilator and less than the second diameter of the cup connection, a second tube extending away from the sheath and terminating in a portion suitable for connecting to one of the inflating syringes, and a terminal outer balloon connected to the second tube, the terminal outer balloon being disposed at one of the distal ends of the sheath, and introducers for introducing each of the balloon guide catheters into a patient.

In accordance with a further feature of the invention, the releasing catheters have a set of hooks adapted to be captured within corresponding stent cells of the vascular prosthesis and to remain adhering thereto throughout a time preceding inflation of the inflatable balloon.

In accordance with an added feature of the invention, each of the releasing catheters have a set of hooks corresponding to a shape of the inflatable balloon and hooks are adapted to be inserted within a corresponding stent of the vascular prosthesis and to remain adhering thereto throughout a time preceding inflation of the inflatable balloon for release.

In accordance with an additional feature of the invention, each of the release catheters has a set of hooks adapted to be inserted within a corresponding stent of the vascular prosthesis for adhering the hooks to the prosthesis.

In accordance with yet another feature of the invention, at least one of the tubes of the releasing catheters is threaded and the connection of at least one of the inflating syringes is correspondingly threaded for connection to the at least one tube.

In accordance with yet a further feature of the invention, the sheath is externally marked, preferably, in centimeters and, in particular, with millimeters as well.

In accordance with yet an added feature of the invention, the sheath has a selective moving ring system adapted to be immobilized on a respective one of the introducers.

In accordance with yet an additional feature of the invention, the sheath has an immobilizer locking the sheath on a respective one of the introducers.

With the objects of the invention in view, there is also provided a method for releasing an aortic prosthesis, including the steps of positioning an introducer in femoral arteries of a patient, providing guiding catheters with depth graduations and balloons, positioning the guiding catheters through the introducers to locate the balloons in terminal parts of common iliac arteries, clamping the proximal aorta, inflating the balloons of the balloon guiding catheters, and opening the aorta, in particular, the aneurysm, accessing from outside the vessel, threading distal ends of the releasing balloon catheters through the guiding catheters and recovering the distal ends of the releasing catheters outside the patient, removing the dilators, moving the prosthesis until distal portions of the releasing catheters contact the guiding catheters, suturing a proximal part of the prosthesis to the aorta, inflating the balloons of the releasing catheters to fix the distal portions of the prosthesis, deflating and extracting the releasing catheters, deflating the balloons of the guiding catheters and removing the guiding catheters, suturing the aorta, in particular, the aneurysm sack, and removing the introducers.

In accordance with again another mode of the invention, guide wires are introduced through the introducers.

In accordance with again a further mode of the invention, a position of the guiding catheters is maintained with the depth graduations viewed on the outside of the introducers.

In accordance with again an added mode of the invention, the releasing catheter threading step is carried out by inserting distal ends of dilators through the guiding catheters, threading the distal ends of the releasing catheters through lumen of the dilators and recovering the distal ends of the releasing catheters outside the patient, and removing the dilators.

In accordance with again an additional mode of the invention, a distance between at least one tip of the dilators and a point for aorto-prosthetic anastomosis is calculated and a length of the vascular prosthesis to be implanted is determined thereby.

In accordance with still another mode of the invention, prosthesis proximal surplus is cut off based upon the length determined.

In accordance with still a further mode of the invention, the aorta incising and suturing steps are carried out by incising and suturing the aneurysm of the aorta.

In accordance with still an added mode of the invention, anchoring stents are disposed at distal portions of the prosthesis and the deployment step is carried out by inflating balloons of the releasing balloon catheters within the stents.

In accordance with an additional mode of the invention, the moving step is carried out by pulling the releasing catheters until the distal portions of the releasing catheters approximately abut against distal ends of the guiding catheters.

In accordance with a concomitant mode of the invention, the lumbar arteries are closed off at the opening of the aorta All in all, the present invention is configured to provide a vascular prosthesis that can be used through a combined laparoscopic/open and endovascular technique. This combined technique is based on the finding that:

conventional suturing of the prosthesis to the "proximal neck" is currently the safest and most provenly effective method for preventing migration of the prosthesis;

the laparoscopic technique reduces invasion and makes it possible to suture a bifurcated prosthesis to the proximal neck of the aorta and suture the lumbar arteries, thus eliminating the problems associated with current traditional techniques; and in the endovascular technique, few complications arise with the sealing of a bifurcated aortic endoprosthesis to the iliac branches.

The device, system, kit, and method of the present invention are not limited to the laparoscopic surgery approach. All fit well and productively within all the new techniques of minimally invasive open surgery.

Other features that are considered as characteristic for the invention are set forth in the appended claims.

Although the invention is illustrated and described herein as embodied in a vascular prosthesis for the treatment of abdominal aortic aneurysms, using a combined laparoscopic/open and endovascular technique and delivery system for releasing a prosthesis fitted with anchoring stents, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figures 1, 2:
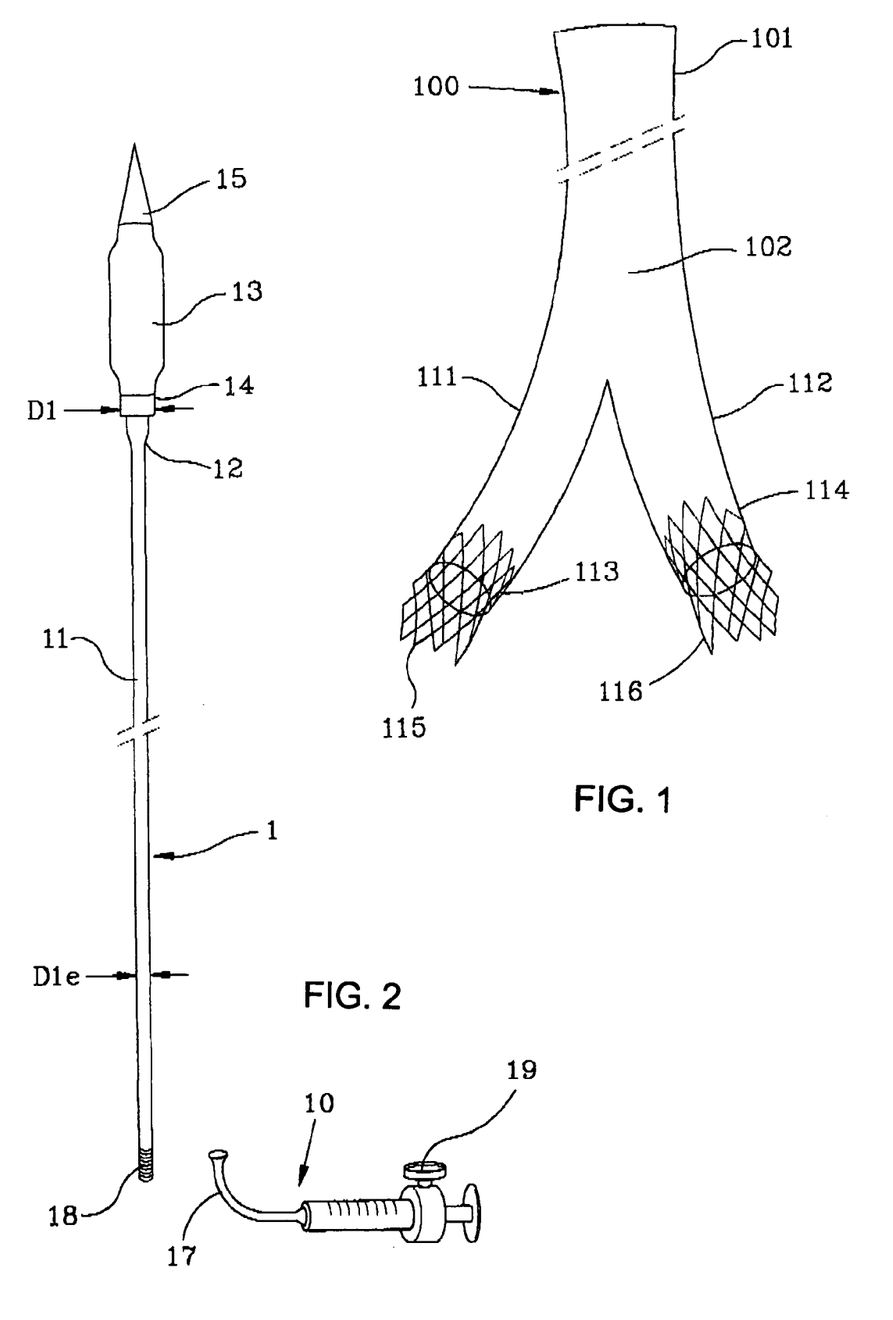
FIG. 1 is a fragmentary, perspective view of a vascular prosthesis for abdominal aortic aneurysm according to the invention.
FIG. 2 is a fragmentary, exploded perspective view of a releasing balloon catheter and a syringe in the delivery system according to the invention.

Referring now to the figures of the drawings in detail and first, particularly to FIG. 1 thereof, there is shown the general appearance of a vascular prosthesis for curing aneurysms of the abdominal aorta, indicated as a whole by reference numeral 100. The prosthesis 100 has a shape of an upside-down Y and includes a tubular body 102 and a pair of tubular branches 111 and 112 diverging downwards from a lower end (not indicated by a reference number) of the tubular body 102. As illustrated in FIG. 1, tubular branches 111, 112 have a diameter smaller than that of body 102, in that, the tubular branches 111, 112 are intended to be received within the iliac arteries, while the body 102 is received within the abdominal aorta at the location of an aneurysm, as will be illustrated below with reference to FIGS. 5 to 10. In particular, tubular body 102 has an upper proximal end 101 that is to be sutured to the proximal neck of the aorta.

Downwardly diverging tubular branches 111, 112 terminate in corresponding distal extremities or portions 113, 114. The prosthesis is constructed of a fabric suitable for vascular use such as DACRON®.

According to the invention, two stents 115, 116, or expandable anchoring systems for holding the prosthesis, are secured to the distal portions 113, 114.

In a conventional way, each stent 115, 116 includes a tubular portion of expandable metal mesh made of a biocompatible material. Each stent 115, 116 is secured to the interior of each distal extremity 113, 114 of branches 111, 112 to be partly covered by the tissue of the prosthesis. In a preferred embodiment, the stent projects by half its length. The stents, of predetermined maximum dimensions (when expanded), are secured to the fabric of branches 111, 112 by suturing or by other measures to permit "crimping" (compression) against a balloon portion of a releasing catheter, as will be discussed below.

In a second aspect, the invention describes a delivery system for releasing a vascular prosthesis as described above to cure an abdominal aortic aneurysm or other vascular and non-vascular prostheses fitted with anchoring stents.

FIG. 2 shows a side view of a releasing balloon catheter 1 and pressure syringe 10. Releasing catheter 1 has a self-supporting small tube 11 with a single lumen for the passage of liquid for inflating the balloon and two opposing ends 12, 18. At end 12 there is a balloon 13 connected to the tube 11 through a cup connection 14 terminating in a head 15. Each balloon 13 is intended to be inserted within a corresponding stent 115, 116 of the vascular prosthesis and to remain adhering thereto throughout the time prior to prosthesis release. A threaded connection is provided at end 18 opposite balloon 13.

Pressure syringe 10 fitted with pressure gauge 19 to achieve controlled inflation of balloon 13 of releasing catheter 1 can be connected to the threaded connection through a correspondingly threaded connection 17. However, connection between the distal portion of small tube 11 and connection 17 of the syringe may be other than by a threaded connection. The releasing catheters come from manufacturers already engaged with the expandable portion of the prosthesis. Any aspect of the delivery system could be sold in separate pieces, but, preferably, the system of the present invention includes the syringes and guiding catheters. In the system for the implantation of prosthesis 100 there is one pair of syringes 10. See, i.e., FIG. 3.

Figure 3:
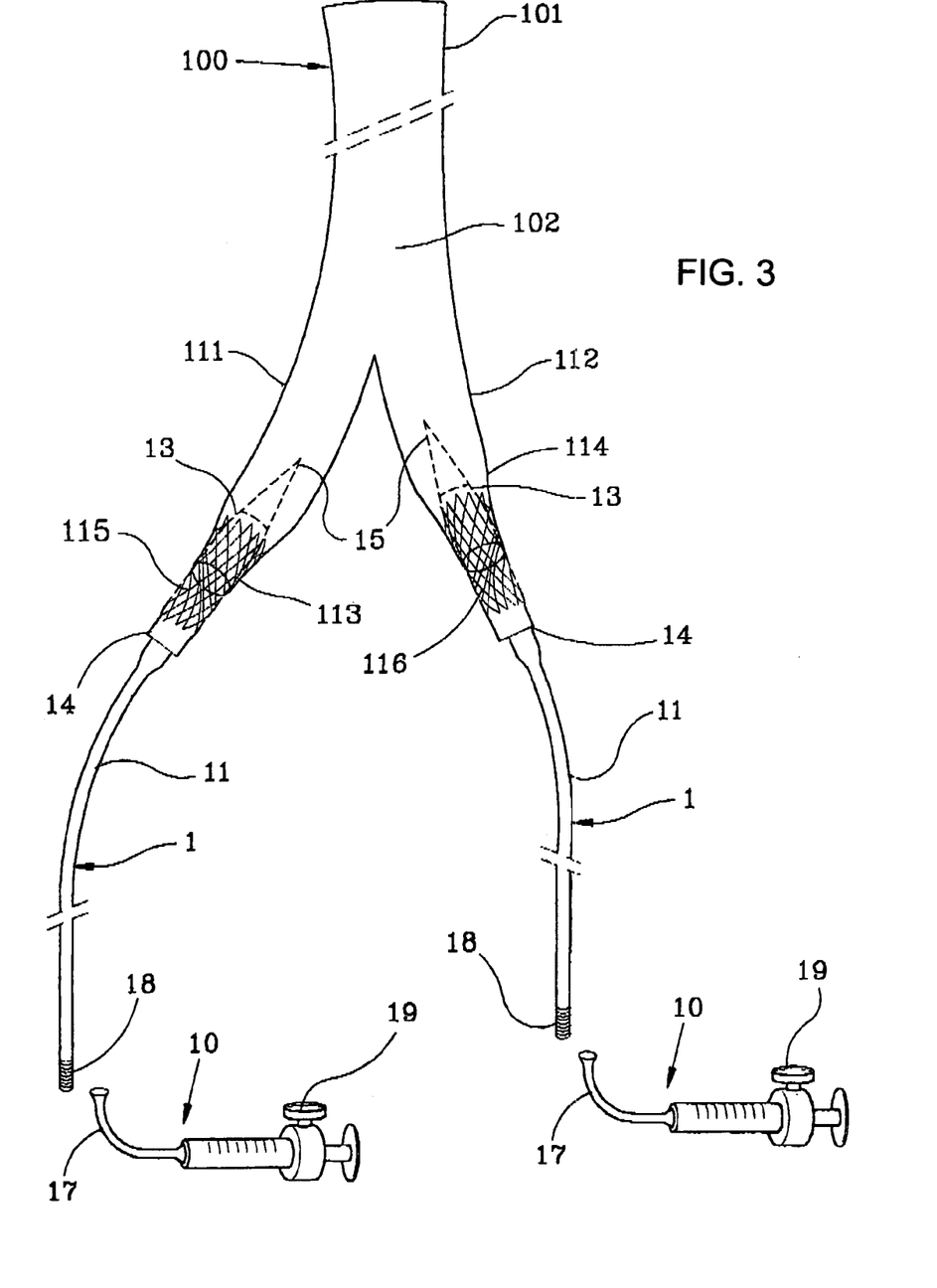
FIG. 3 is a fragmentary, exploded perspective view of the vascular prosthesis of FIG. 1 connected to a pair of the releasing catheters and syringes of FIG. 2.

Releasing catheter 1 is associated with prosthesis 100 through its balloon 13 within the corresponding stents 115, 116 of prosthesis 100 such that there is structural continuity between catheter 1 and prosthesis 100. In fact, catheter 1 and branches 113, 114 of prosthesis 100 become one piece through the effect of compressing the stent 115, 116 against the balloon 13 of the catheter 1.

Figures 4, 5:
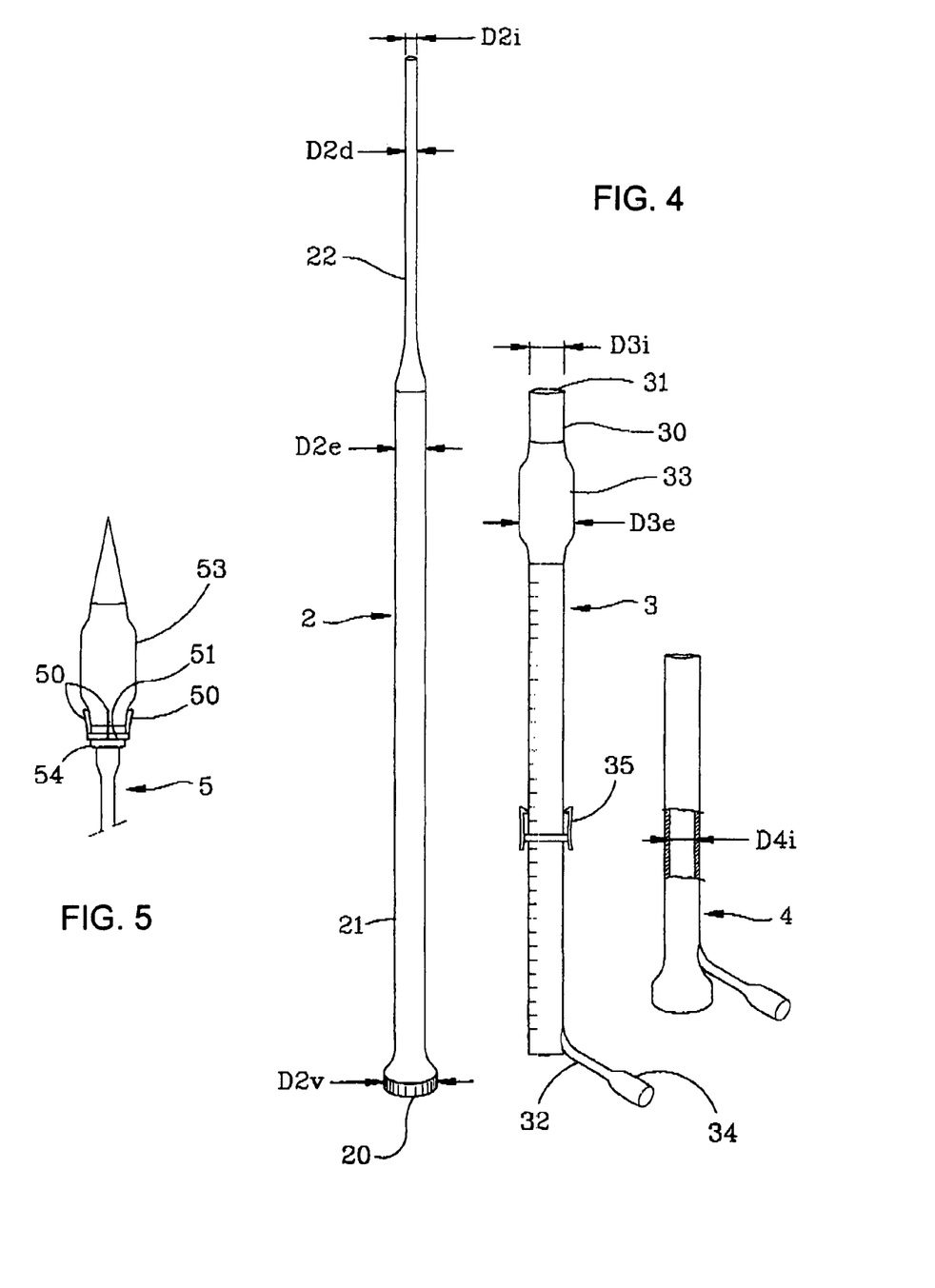
FIG. 4 is a perspective view of a guiding balloon catheter, including a conventional valve introducer, forming part of the delivery system kit according to the invention.
FIG. 5 is a fragmentary, side elevational view of an alternative embodiment of the releasing balloon catheter according to the invention.

In a variant illustrated in FIG. 5, which is a partial frontal view of a releasing catheter 5, provision is made for a series of hooks 50 incorporated with the cup connection for balloon 54, for example, through a sheath 51 on which they are hinged.

Hooks 50, which can number three or four, made of a material similar to that of the catheter, have points facing inward and are intended to engage the mesh of the stent compressed on balloon 54. Hooks 50 may act as an aid to prevent the balloon 54 from being drawn along by the stent during traction, adhering to the mesh of the stent 115, 116. Of course, hooks 50 will cease to engage the stent 115, 116 when the balloon 54 is inflated and deflated for release of the prosthesis 100.

At rest, and, therefore, in a closed conformation, the stents 115, 116 are compressed onto the balloons 13, 54 of the balloon catheters 1, 5. For such a purpose, the length of the stent 115, 116 corresponds to the length of the isometric portion of the balloon as shown in FIG. 3.

The small tube 11 of the releasing balloon catheter 1 has an external diameter D1e (FIG. 2), while its cup connection 14 with balloon 13 has a diameter D1, again measured externally. Diameter D1 is greater than diameter D1e.

The tube 11 of releasing catheter 1 (preferably, of a conventional plastic material) allows the liquid filling balloon 13 to pass therethrough and to inflate the balloon 13 under pressure. In the proximal portion corresponding to the balloon 13, the cup connection 14 has a shoulder with an outer diameter D1, for example, approximately equal to 2 mm. This diameter is substantially identical to diameter D3i (see FIG. 4) to form an abutting contact. The small tube 11 has an external diameter D1e of approximately 1.35 mm and a length of approximately 0.60 to 1.5 m, by way of example.

With reference to FIG. 4, three components of the delivery system are illustrated that have a function of guiding the releasing balloon catheter, together with guiding wires and syringes not illustrated in FIG. 4. In particular, FIG. 4 shows a guiding balloon catheter including a dilator 2 and a sheath 3. The guiding catheter works in a conventional introducer 4.

Dilator 2 has a tubular structure with a proximal portion 20, a median portion 21, and a distal portion 22. Proximal portion 20, which has a larger outside diameter D2v, is provided with a haemostatic valve. Median portion 21 has a constant outside diameter D2e that is less than that of proximal portion D2v, while distal portion 22, which is tapered and elongated for entry into the aorta and to reach the aneurysmatic portion, has a minimum diameter D2d.

Dilator 2 has an inner lumen of diameter D2i that is suitable for passage of the small tube 11 of the releasing catheter 1 (which has an outside diameter D1e, for example of 1.35 mm, as mentioned above).

Sheath 3 is external and supplementary to median portion 21 of dilator 2, as a result, the dilator 2 projects from the sheath by some 10 to 15 cm. The sheath 3 is made of a suitable plastic material and has the shape of a tube 30 of maximum outside diameter D3e. Sheath 3 has a central channel 31 of inside diameter D3i suitable for the passage of dilator 2 and substantially identical to the diameter D1 of the releasing catheter 1, and an eccentric channel 32 for inflating a balloon 33 located at the distal end of sheath 3. Balloon 33 can be inflated by liquid and is made of a compliant plastic material of approximately one centimeter's length. When inflated, balloon 33 takes up an elliptical shape, with a major diameter D3e that is transverse to the axis of sheath 3 and that varies, for example, from 10 mm to 14 mm. The distal part of balloon 33 is located approximately 2 mm from the end of sheath 3. The liquid is delivered to balloon 33 through the eccentric channel 32 that terminates at the proximal extremity in a syringe connection 34. The outside of the sheath 3 is graduated in centimeters, i.e., it is notched and/or numbered so that the depth to which it is introduced can be determined, as will be discussed below. For convenience in use, a movable ring with an immobilizing system 35 of the traditional spring-loaded ratchet type may be present on the outside of the sheath to mark the point at which the sheath 3 exits from introducer 4.

The guiding balloon catheter complex including dilator 2 and sheath 3 is compatible with a conventional introducer 4 of suitable size.

Introducer 4 has an inside diameter D4i, conventionally of 7 French (2.3 mm), to allow the passage of the sheath 3 having a slightly smaller outside diameter D3e. Sheath 3 has an inside diameter D3i, for example of 2 mm, to allow dilator 2 having a diameter D2e, which is slightly less than the inside diameter D3i of the sheath, to pass. As already mentioned, within dilator 2 there is a constant lumen of diameter D2i that is slightly greater than the outside diameter D1 of small tube 11 of the releasing catheter 1.

An example of the release of the vascular prosthesis 100 according to the present invention through the use of the delivery system including releasing balloon catheters 1 and guiding catheters (dilator 2, sheath 3) and the surgical kit including the syringes and introducers and, possibly, the prosthesis 100 as well, according to the present invention is provided below with reference to FIGS. 6 to 12, which are diagrammatical views of a region where the prosthesis 100 is released and the corresponding system. Release is made possible by a combined laparoscopic/open and endovascular technique for curing aneurysms of the abdominal aorta developed by the inventors of the present invention.

Prosthesis 100 is configured to be introduced through a small incision in a patient's abdomen. The proximal part of prosthesis 100 is cut off according to need and measurements taken "in vivo" and from tomography scans.

FIGS. 6 to 12 diagrammatically show the abdominal aorta affected by an aneurysm A below the proximal neck C of the aorta. AC indicates the common iliac artery, AE the external iliac artery, AF the femoral artery, and AI the hypogastric arteries.

Figure 6:
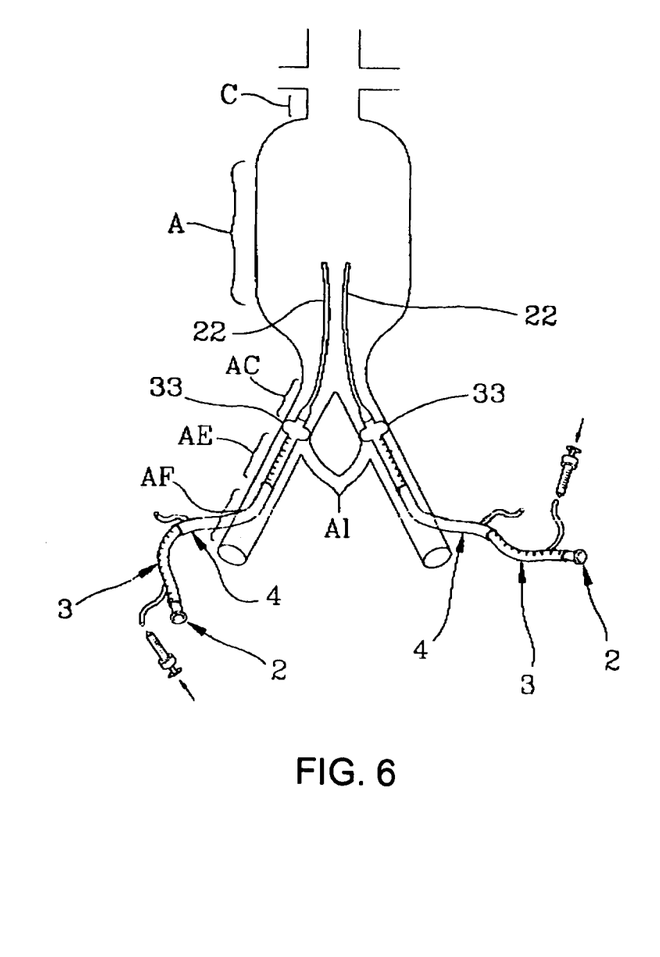
FIGS. 6 to 12 are fragmentary, perspective diagrammatical views of an aneurysm of the abdominal aorta during successive stages of implantation of the prosthesis of FIG. 1 in a method according to the invention.
Figure 7:
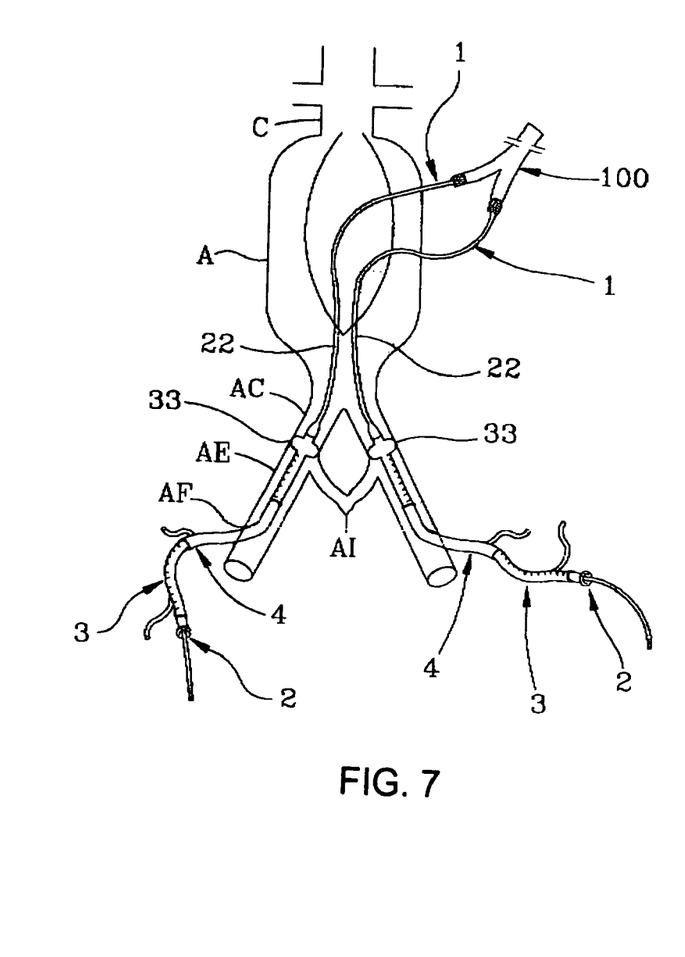

As shown in FIG. 6, conventional introducers 4, fitted with valves, are positioned by percutaneous puncture of the femoral arteries AF. Through the introducers 4, non-illustrated guide wires are introduced with the help of radioscopy. Guiding catheters 3 with balloons 33 are positioned on the introducers 4 such that the balloons 33 are located in the terminal parts of the common iliac arteries AC. The corresponding number that can be seen on the outside of introducer 4 in such a position is marked, which makes it possible to maintain the correct position throughout the procedure without the need for radiological monitoring (see FIG. 6). The proximal aorta is clamped and balloons 33 of guiding catheters 3 are inflated. At the opening of the aorta, as shown in FIG. 7, the lumbar arteries are closed off and the ends of dilators 2 are inserted. Because they are of a fixed length, the distance between their tips and a suitable point for aortoprosthetic anastomosis can be calculated, and, thus, the necessary length of the vascular prosthesis can be determined and the surplus at the proximal end can be cut off. As an alternative, small tubes 11 are fitted onto the tapering distal portions 22 of dilators 2 (FIG. 7), recovering them outside the patient, dilators 2 are extracted (FIG. 8) and the prosthesis 100 is moved until it comes to a stop through contact between the cup 14 of the releasing catheters 1 and the distal ends of the guiding catheters 3, and, then, the surplus proximal part of the prosthesis 100 is cut off. The proximal part of the prosthesis 100 is, then, sutured to the proximal neck C of the aorta using conventional methods (FIG. 9), where numeral 6 indicates needles for suturing or where suturing will be performed in the future, with automatic staplers, for example.

Figure 8:
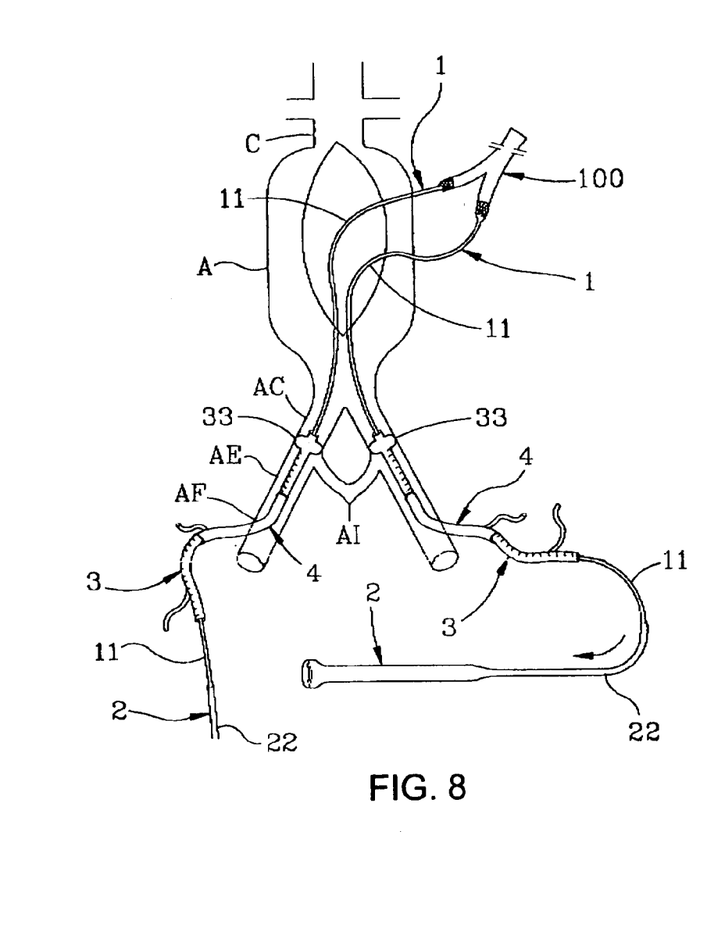
Figure 9:
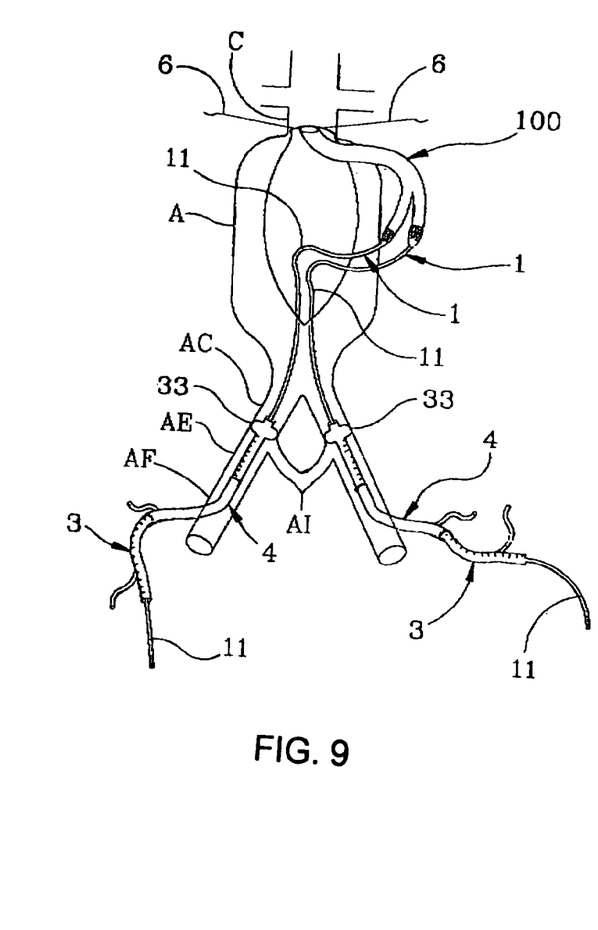
Figure 10:
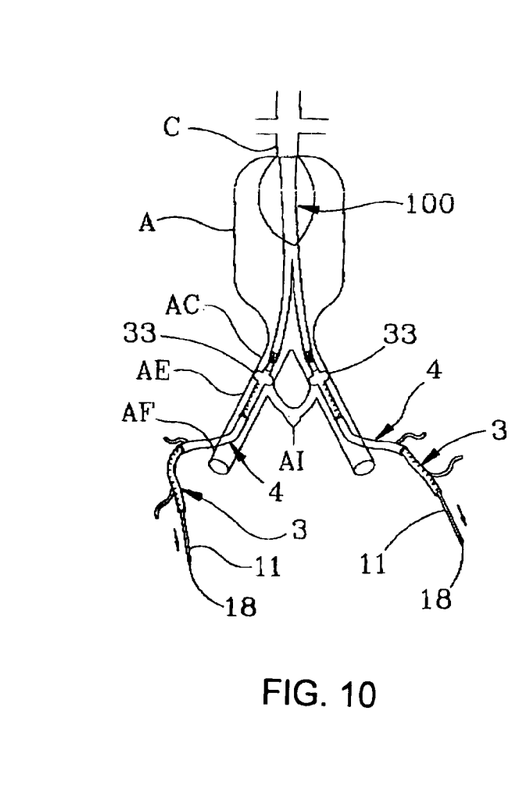
Figure 11:
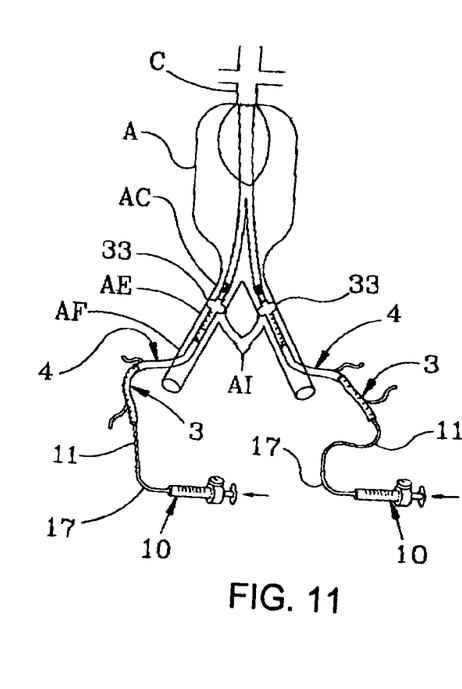

Once the anastomosis has been completed and its leaktightness has been checked, if this has not been done previously, the distal ends of the releasing catheters 1 are introduced into the lumens of the guiding catheters, removed to the exterior and recovered, and dilators 2 are extracted from them (FIG. 8). Then, the ends of the two releasing catheters 1 are carefully pulled until cup connections 14 of the releasing catheter 1 abut against the ends of sheath 3 of the guiding catheters (FIG. 10). The terminal portions 18 of catheters 1 are screwed into connections 17 of syringes 10 with pressure gauges, balloons 13 of releasing catheters 1 are inflated and, thereafter, the stents 115, 116 are released (FIG. 11).

Figure 12:
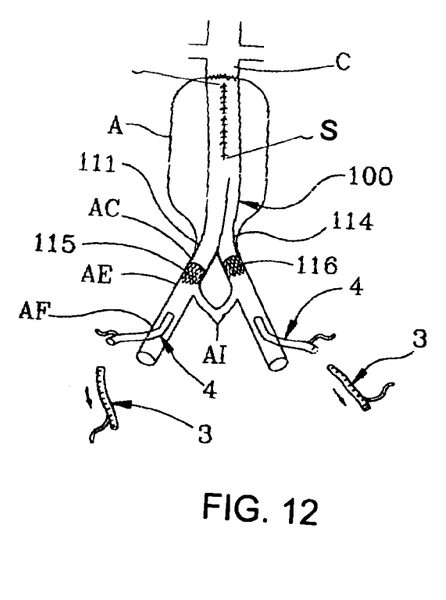

At this point balloons 13 are deflated, balloon catheters 1 are extracted, and, then, balloons 33 are deflated and the sheaths 3 of the guiding catheters are withdrawn. A check is made to ensure that the stents 115, 116 are correctly positioned and that they are leaktight, and, then, suturing S of the aneurysm part A of the aorta is performed (FIG. 12). Upon completion, an angiographic check can be performed and introducers 4 in the femoral arteries can be removed.

Using the combined laparoscopic/open and endovascular technique described above, which is made possible by the present invention, the problems associated with conventional surgery and the complications and consequences of a long median abdominal incision, such as post-operative pain, dynamic ileum (lack of digestive movements of the intestine for 4–5 days), immobility, and respiratory complications are mitigated.

Using the technique described above, which is made possible by the present invention, problems that may follow the mere endovascular exclusion of aneurysms of the abdominal aorta can also be overcome. The problems overcome include:

migration of the prosthesis as a result of its suture to the stump of the aorta;

endo-leaks due to loss of seal at the proximal supporting points (Type I) because of the proximal surgical suture and the low probability of movement and loss of adhesion of the stents in the iliac arteries;

endo-leaks due to all the arteries that might give rise to reflux bleeding (lumbar and inferior mesenteric arteries) (Type II), given that these arteries are sutured directly;

endo-leaks due to disconnection (Type III) of the various modules, as this is a single body prosthesis;

the need for large introducers for femoral access, it being possible to perform the endovascular part wholly percutaneously (i.e., without incision); and reduced exposure to radiation, in that, the presence of centimeter-graduated guiding catheters makes it possible to position the catheters under radiological guidance once only, at the start of the procedure, and positioning of the distal part of the prosthesis can be completed merely by nesting the releasing catheters in the guiding catheter sheaths (of the same diameter).

Using the technique described above, made possible by the present invention, problems associated with the laparoscopic technique alone, such as the elimination of sutures in the iliac branches and the possibility of making a single anastomosis, which appreciably reduces the time required for the reconstructive stage of surgery, are also overcome.

The prosthesis according to the invention will be made in various sizes, with various stent diameters (as regards the measurement of maximum expansion) and various balloon diameters for the releasing catheter, according to the requirements of the patient for whom it is intended.

The present invention has been described with reference to a specific embodiment, but it must be expressly understood that modifications, admissions, and/or omissions may be made without thereby going beyond the corresponding scope of the protection defined by the appended claims.

We claim:

1. A delivery system for release of a prosthesis having anchoring stents, comprising:

a pair of releasing balloon catheters each having:

an inflatable balloon adapted to be inserted within a corresponding stent of the prosthesis and to continue adhering thereto throughout a time prior to release thereof;

a self-supporting tube defining a single lumen and having a first diameter and two opposing ends;

a cup connection having a second diameter greater than said first diameter, said cup connection being disposed at a first of said ends, fluidically connecting said lumen with said inflatable balloon, and connecting said inflatable balloon to said tube for passing liquid to inflate said inflatable balloon; and a terminal connection fluidically connected to said lumen at a second of said ends;

a pair of inflating syringes each having a connection for releasable attachment to said terminal connection of a respective one of said releasing catheters and for fluidically connecting a respective one of said syringes to said inflatable balloon to inflate said inflatable balloon and thereby release a respective stent;

a pair of guiding balloon catheters each having:

a dilator defining an inner lumen having an inner third diameter sized to pass said tube of said releasing catheter therethrough, said dilator having:

a proximal portion having an outer fourth diameter larger than said inner third diameter and being fitted with a haemostatic valve;

a median portion having a substantially constant outer fifth diameter smaller than said outer fourth diameter; and an elongated distal portion tapering for retrieval in an aorta; and a tubular sheath having:

distal ends;

an inner sixth diameter at least as great as said outer fifth diameter of said median portion of said dilator and less than said second diameter of said cup connection;

a second tube running eccentrically outside said sheath and terminating in a portion for connection to one of said inflating syringes; and a terminal outer balloon connected to said second tube, said terminal outer balloon being disposed at one off said distal ends of said sheath; and introducers fitted with valves for each of said guiding catheters.

2. The delivery system according to claim 1, wherein each of said releasing catheters has a set of hooks adapted to be captured within a corresponding stent of the vascular prosthesis and to remain adhering thereto throughout a time preceding inflation of said inflatable balloon.

3. The delivery system according to claim 1, wherein:

each of said releasing catheters has a set of hooks corresponding to a shape of said inflatable balloon; and said hooks are adapted to be captured within the corresponding stent of the prosthesis and to remain adhering thereto throughout a time preceding inflation of said inflatable balloon for release.

4. The delivery system according to claim 1, wherein:

said tube of said releasing catheters is threaded; and said connection of each of said inflating syringe is correspondingly threaded for connection to said tube.

5. The delivery system according to claim 1, wherein said sheath is externally marked in centimeters and has a selective moving ring system adapted to be immobilized on a respective one of said introducers.

6. The delivery system according to claim 1, wherein said sheath is externally marked in centimeters and has an immobilizer locking said sheath on a respective one of said introducers.

7. A delivery system for releasing a prosthesis having anchoring stents, comprising:

a pair of releasing balloon catheters each having:

an inflatable balloon adapted to be removably inserted within a portion of the prosthesis;

a self-supporting tube defining a lumen and having a first diameter and two opposing ends;

a cup connection having a second diameter greater than said first diameter, said cup connection being disposed at a first of said ends and connecting said inflatable balloon to said tube to fluidically connect said lumen with said inflatable balloon to pass liquid to inflate said inflatable balloon; and a terminal connection fluidically connected to said lumen at a second of said ends;

a pair of inflating syringes each having a connection for releasable attachment to said terminal connection of a respective one of said releasing catheters and, when connected thereto, fluidically connecting a respective one of said syringes to said inflatable balloon;

a pair of guiding balloon catheters each having:

a dilator defining an inner lumen having an inner third diameter sized to pass said tube of said releasing catheter therethrough, said dilator having:

a proximal portion having an outer fourth diameter larger than said inner third diameter;

a median portion having a substantially constant outer fifth diameter smaller than said outer fourth diameter; and a distal portion tapering for insertion into a vessel; and a tubular sheath having:

distal ends;

an inner sixth diameter at least as great as said outer fifth diameter of said median portion of said dilator and less than said second diameter of said cup connection;

a second tube extending away from said sheath and terminating in a portion for connection to one of said inflating syringes; and a terminal outer balloon connected to said second tube, said terminal outer balloon being disposed at one of said distal ends of said sheath; and introducers for introducing each of said guiding catheters into a patient.

8. The delivery system according to claim 7, wherein each of said releasing catheters has a set of hooks adapted to be captured within a corresponding stent of the vascular prosthesis for adhering said hooks to the prosthesis.

9. The delivery system according to claim 7, wherein:

at least one of said tubes of said releasing catheters is threaded; and said connection of at least one of said inflating syringes is correspondingly threaded for connection to said at least one tube.

10. The delivery system according to claim 7, wherein said sheath is externally marked.

11. The delivery system according to claim 10, wherein said sheath has a selective moving ring system adapted to be immobilized on a respective one of said introducers.

12. The delivery system according to claim 10, wherein said sheath has an immobilizer locking said sheath on a respective one of said introducers.

* * * * *